US011918017B2

(12) United States Patent
Ahlvers et al.

(10) Patent No.: US 11,918,017 B2
(45) Date of Patent: Mar. 5, 2024

(54) SANITIZING PROCESS FOR EXPOSING A FOOD CONTAINER TO MULTIPLE SANITIZING AGENTS ALONG A CIRCUITOUS PATH

(71) Applicant: Incuvator Fund I, LLC, Sabetha, KS (US)

(72) Inventors: Cole M. Ahlvers, Topeka, KS (US); Eric J. Spurgeon, Buhler, KS (US); John C. Kuenzi, Sabetha, KS (US)

(73) Assignee: Incuvator Fund I, LLC, Sabetha, KS (US)

( * ) Notice: Subject to any disclaimer, the term of this patent is extended or adjusted under 35 U.S.C. 154(b) by 0 days.

(21) Appl. No.: 18/065,609

(22) Filed: Dec. 13, 2022

(65) Prior Publication Data
US 2023/0113928 A1 Apr. 13, 2023

Related U.S. Application Data

(62) Division of application No. 15/733,734, filed as application No. PCT/US2019/027206 on Apr. 12, 2019, now Pat. No. 11,559,069.
(Continued)

(51) Int. Cl.
*A61L 2/00* (2006.01)
*A23B 4/03* (2006.01)
(Continued)

(52) U.S. Cl.
CPC .............. *A23L 3/001* (2013.01); *A23L 3/28* (2013.01); *A23L 3/34095* (2013.01);
(Continued)

(58) Field of Classification Search
CPC ... A23L 2/107; A23L 3/28; A23L 3/00; A23L 3/001
(Continued)

(56) References Cited

U.S. PATENT DOCUMENTS 3,996,386 A 12/1976 Malkki et al.
4,606,262 A 8/1986 Robinson, Jr. et al.
(Continued)

FOREIGN PATENT DOCUMENTS

CA 2457083 A1 1/2005
EP 0899195 A1 3/1999
(Continued)

OTHER PUBLICATIONS

Austin Donner, Investigation of In-Package Ozonation, Journal of Purdue Undergraduate Research, Fall 2011, 6 pages, vol. 1, Purdue University, Indiana, United States.
(Continued)

*Primary Examiner* — Monzer R Chorbaji
(74) *Attorney, Agent, or Firm* — Coughlin Law Office LLC; Daniel J. Coughlin; Stuart M. Aller

(57) ABSTRACT

A method for sanitizing pre-measured units of a pre-sanitized flowable food product in a sanitizing device installed into an existing food production system without substantially increasing the head height requirement of the feed production system. A plurality of containers are moved about a path with increased retention time through a plurality of stations: a receiving station, one or more sanitizing stations, and a dispensing station, and a container cleaning station. A pre-measured unit measured for packaging is received at the receiving station into a container. The pre-measured unit is exposed to one or more sanitizing agents at one or more sanitizing stations. The pre-measured unit is immediately packaged after sanitization. The pre-measured unit is dispensed into a packaging device at the dispensing station. The containers are then cleaned at the container cleaning station to prepare each container to receive a subsequent pre-measured unit of the pre-sanitized flowable feed product.

20 Claims, 12 Drawing Sheets

Related U.S. Application Data

(60) Provisional application No. 62/657,422, filed on Apr. 13, 2018.

(51) Int. Cl.

| | |
|---|---|
| *A23L 3/00* | (2006.01) |
| *A23L 3/28* | (2006.01) |
| *A23L 3/3409* | (2006.01) |
| *A23L 3/3445* | (2006.01) |
| *A61L 2/10* | (2006.01) |
| *A61L 2/12* | (2006.01) |
| *A61L 2/20* | (2006.01) |
| *B65B 1/06* | (2006.01) |
| *B65B 55/14* | (2006.01) |
| *B65B 55/16* | (2006.01) |
| *B65B 55/18* | (2006.01) |

(52) U.S. Cl.
CPC ............... *A23L 3/3445* (2013.01); *A61L 2/10* (2013.01); *A61L 2/12* (2013.01); *A61L 2/202* (2013.01); *B65B 1/06* (2013.01); *B65B 55/14* (2013.01); *B65B 55/16* (2013.01); *B65B 55/18* (2013.01); *A23V 2002/00* (2013.01)

(58) Field of Classification Search
USPC .............. 422/22, 24, 28, 292, 307; 426/443; 99/516, 473
See application file for complete search history.

(56) References Cited

U.S. PATENT DOCUMENTS

| | | | |
|---|---|---|---|
| 4,974,503 A | 12/1990 | Koch | |
| 5,613,428 A | 3/1997 | Kendall et al. | |
| 6,150,663 A | 11/2000 | Rosenthal | |
| 6,349,526 B1 | 2/2002 | Newman | |
| 6,692,684 B1 | 2/2004 | Nantin et al. | |
| 6,719,015 B2 | 4/2004 | Murray | |
| 7,160,566 B2 | 1/2007 | Fink et al. | |
| 7,205,016 B2 | 4/2007 | Garwood | |
| 7,955,631 B2 | 6/2011 | Turatti | |
| 8,012,521 B2 | 9/2011 | Garwood | |
| 8,181,431 B2 | 5/2012 | Py et al. | |
| 8,252,230 B2 | 8/2012 | Benson et al. | |
| 8,966,866 B2 | 3/2015 | Py | |
| 2003/0091708 A1 | 5/2003 | Garwood | |
| 2004/0056201 A1 | 3/2004 | Fink et al. | |
| 2004/0081729 A1 | 4/2004 | Garwood | |
| 2004/0146602 A1 | 7/2004 | Garwood et al. | |
| 2006/0127545 A1 | 6/2006 | Newman | |
| 2007/0154600 A1 | 7/2007 | Parry et al. | |
| 2007/0254074 A1 | 11/2007 | Garwood | |
| 2008/0166694 A1 | 7/2008 | Weber et al. | |
| 2009/0304880 A1 | 12/2009 | Kidder et al. | |
| 2009/0311392 A1 | 12/2009 | Newman | |
| 2010/0257820 A1 | 10/2010 | Doll et al. | |
| 2013/0302490 A1* | 11/2013 | James | A23B 7/0053 426/443 |
| 2014/0161663 A1 | 6/2014 | Farren et al. | |
| 2015/0305396 A1 | 10/2015 | Cottone | |

FOREIGN PATENT DOCUMENTS

| | | | |
|---|---|---|---|
| GB | 2181205 | A | 4/1987 |
| JP | H08308478 | A | 11/1996 |
| JP | 2005027657 | A | 2/2005 |
| WO | 8803369 | A1 | 5/1988 |
| WO | 9115969 | A1 | 10/1991 |
| WO | 9319629 | A1 | 10/1993 |
| WO | 9427868 | A2 | 12/1994 |
| WO | 9816428 | A1 | 4/1998 |
| WO | 2006108453 | A1 | 10/2006 |
| WO | 2014128470 | A2 | 8/2014 |

OTHER PUBLICATIONS

Craig R Bonneville, Nelly Feze, Gary Lee Hahn, Robert E Hanson, Vernonn D Farman, Tou T Vang,アール．ボンネビル クノンイー．ハンソン ロバート．レイグリー ハーン ゲイリーティ ィー，バング トウフェゼ ネリーディー．カーマン バー ，"Surface pasteurizing method", published on Feb. 3, 2005 as JP2005027657A, this is a Machine Translated Text.

Narcisco Lagares-Corominas, ナールシソ・ラガレス・コロミナス,"Automatic machine for sterilization and aseptic packaging of meat product", published on Nov. 26, 1996 as JPH08308478A, this is a Machine Translated Text.

Shane Thomas, International Search Report, dated Jun. 13, 2019, 23 pages.

Soon Kiat Lau and Jeyamkondan Subbiah, Ph.D., P.E., Radio Frequency Heating for Low-Moisture Foods, Food Safety Magazine, Jun./Jul. 2017, 7 pages, United States.

Thomas, Shane, Authorized Officer, International Search Report, dated Jun. 28, 2019, 2 pages, published online.

* cited by examiner

FIG. 9
900

```
┌─────────────────────────────────────────────────────────────────────────────┐
│ Positioning a first container at the filling station, wherein the first     │
│ container comprises an open space between a first plug and a second plug    │
│ of a drag chain conveyor                                               902  │
└─────────────────────────────────────────────────────────────────────────────┘
                                      ↓
┌─────────────────────────────────────────────────────────────────────────────┐
│ Receiving a first unit of a flowable food product directly into the first   │
│ container at a filling station, the first unit being discrete and           │
│ pre-measured                                                           904  │
└─────────────────────────────────────────────────────────────────────────────┘
                                      ↓
┌─────────────────────────────────────────────────────────────────────────────┐
│ Moving the first unit in the first container along a path             906  │
└─────────────────────────────────────────────────────────────────────────────┘
                                      ↓
┌─────────────────────────────────────────────────────────────────────────────┐
│ Providing an ultraviolet light source to generate an ultraviolet radiation  │
│ as the first sanitizing agent                                          908  │
└─────────────────────────────────────────────────────────────────────────────┘
                                      ↓
┌─────────────────────────────────────────────────────────────────────────────┐
│ Exposing the first unit to the first sanitizing agent at a first            │
│ sanitizing station disposed along the path                             910  │
└─────────────────────────────────────────────────────────────────────────────┘
                                      ↓
┌─────────────────────────────────────────────────────────────────────────────┐
│ Admitting the ultraviolet radiation into the first container through a      │
│ wall of the first container                                            912  │
└─────────────────────────────────────────────────────────────────────────────┘
                                      ↓
┌─────────────────────────────────────────────────────────────────────────────┐
│ Flooding the first container with a fluid sanitizing agent at a second      │
│ sanitizing station disposed along the path                             914  │
└─────────────────────────────────────────────────────────────────────────────┘
                                      ↓
┌─────────────────────────────────────────────────────────────────────────────┐
│ Admitting the fluid sanitizing agent into the first container through a     │
│ plurality of perforations in a wall of the first container             916  │
└─────────────────────────────────────────────────────────────────────────────┘
                                      ↓
┌─────────────────────────────────────────────────────────────────────────────┐
│ Exposing the first container to a discharge aperture to dispense the first  │
│ unit of the flowable food product under the force of gravity           918  │
└─────────────────────────────────────────────────────────────────────────────┘
                                      ↓
┌─────────────────────────────────────────────────────────────────────────────┐
│ Dispensing the first unit from the first container for subsequent packaging │
│ at a dispensing station disposed along the path                        920  │
└─────────────────────────────────────────────────────────────────────────────┘
                                      ↓
┌─────────────────────────────────────────────────────────────────────────────┐
│ Returning the first container to the filling station for refilling with a   │
│ second unit of the flowable food product                               922  │
└─────────────────────────────────────────────────────────────────────────────┘
```

| Moving a plurality of containers about a path within a housing, the path comprising a receiving station, a sanitizing station, and a dispensing station, wherein the receiving station is adjacent to the dispensing stations    1002 |
|---|
| Receiving a pre-measured unit of the flowable food product at the receiving station into a first container    1004 |
| Exposing the pre-measured unit of the flowable food product to two or more sanitizing agents at the sanitizing station    1006 |
| Dispensing the pre-measured unit of the flowable food product from the first container at the dispensing station    1008 |
| Repeating the steps of receiving, exposing, and dispensing for successive pre-measured units of the flowable food product within the first container    1010 |

1100

| Receive a first unit of a flowable food product directly into a first container at a filling station, the first unit being a discrete quantity measured for packaging |
| --- |
| 1102 |

↓

| Circuit the first unit in the first container along a path |
| --- |
| 1104 |

↓

| Expose the first unit to a first sanitizing agent at a first sanitizing station disposed along the path |
| --- |
| 1106 |

↓

| Dispense the first unit from the first container at a dispensing station disposed along the path |
| --- |
| 1108 |

↓

| Return the first container to the filling station for refilling with a second unit of the flowable food product. |
| --- |
| 1110 |

```
┌─────────────────────────────────────────────────────────────┐
│ Receive a first unit of the plurality of units of the        │
│ flowable food product at the receiving station into a        │
│ first container                                              │
│ 1202                                                         │
└─────────────────────────────────────────────────────────────┘
                              ↓
┌─────────────────────────────────────────────────────────────┐
│ Sanitize the first unit of the flowable food product with    │
│ a sanitizing agent at the sanitizing station                 │
│ 1204                                                         │
└─────────────────────────────────────────────────────────────┘
                              ↓
┌─────────────────────────────────────────────────────────────┐
│ Dispense the first unit of the flowable food product from    │
│ the first container at the dispensing station                │
│ 1206                                                         │
└─────────────────────────────────────────────────────────────┘
                              ↓
┌─────────────────────────────────────────────────────────────┐
│ Repeat the steps of receiving, exposing, and dispensing for  │
│ a second unit of the flowable food product within the first  │
│ container.                                                   │
│ 1208                                                         │
└─────────────────────────────────────────────────────────────┘
```

FIG. 12

SANITIZING PROCESS FOR EXPOSING A FOOD CONTAINER TO MULTIPLE SANITIZING AGENTS ALONG A CIRCUITOUS PATH

CROSS REFERENCES

This application is a divisional of U.S. National Phase application Ser. No. 15/733,734, entitled "Sanitizing Package-Ready Pre-Quantified Units of Food", and filed on 9 Oct. 2020, which is the National Stage of Patent Cooperation Treaty Application No. PCT/US2019/027206, entitled "Sanitizing Package-Ready Pre-Quantified Units of Food", and filed on 12 Apr. 2019, which claims benefit of U.S. Provisional Application No. 62/657,422, entitled "Continuous Food Sanitizing Process", and filed on 13 Apr. 2018.

FIELD OF THE INVENTION

The present disclosure relates to sanitizing pre-quantified units of food immediately prior to packaging.

BACKGROUND

Product recalls is one of the biggest concerns in the food and feed industry. The presence of pathogens such as *E. Coli, Salmonella*, and *Listeria* can result in factory shut-downs, product recalls, legal penalties, and liability. Extrusion-based kill-steps are a validated method ensuring the destruction of pathogenic microorganisms. These sanitizing steps provide a measured amount of reduction in the presence of these pathogens, which is generally measured in "log reductions."

However, after the initial extrusion-based sanitizing step, additional processing and packaging can introduce new contaminants. Whether introduced from a worker or the environment, additional pathogens introduced into the food or feed product after the initial sanitizing step can also result in pathogen-infected foods or feed leaving the facility.

SUMMARY

We disclose a sanitizing device that provides volumetric holding of discrete, pre-weighed units of a flowable product in an enclosed environment. Existing food facilities suffer the problem of environmental or user contamination of the food within the facility past the initial pathogen kill step. We eliminate the opportunity for subsequent contamination by providing a sanitizing step immediately prior to the packaging step. The pre-quantified food resides within a container that travels along a path through one or more sanitizing stations. At a dispensing station, the re-sanitized contents of the container as discharged directly into the packaging device.

Prior to packaging, the flowable food products may be weighed or measured for sale. We recognized that flowable products can be maintained in these discrete pre-quantified units while being exposed to the appropriate sanitizing agents immediately before packaging. The containers maintain the quantity of the pre-quantified units so that the discrete units are ready to be packaged upon discharge from the sanitizing device. This prevents opportunities for recontamination after leaving the sanitizing device.

The sanitizing device is designed to be compatible with existing food production facilities. It is often inconvenient and costly for a facility to raise its production equipment—such as extruders, conveyors, and other processing equipment—higher in the facility. We realized that the path could be configured to increase the residence time of the flowable product with the sanitizing agent without interfering with other components within the production facility. The path may extend horizontally, maintaining the unit of the flowable food product inside the path and being exposed to a sanitizing agent during the duration of the movement through the path. The container can then return adjacent to the filling station to dispense the flowable food product into the packaging device without requiring a substantial change to the design of the facility.

Pathogens can become resistant to sanitizing agents over time. We recognized that one or more sanitizing stations could be disposed along the container's path to expose the flowable food product to a plurality of sanitizing agents. The sanitizing agent introduced at each sanitizing station is determined based on the food product to be sanitized. The sanitizing agent may include heat, chemical, or irradiation. Two or more sanitizing agents may be simultaneously or sequentially introduced in order to increase the efficacy of the individual sanitizing agents, minimize any deleterious affect on the food product, minimize the residence time required for the food product in the sanitizing device, and to prevent resistant pathogens from developing within the system.

Some types of sanitizing agents are incompatible with the packaging material. In order to expose the flowable food products to these sanitizing agents, the pre-quantified units of flowable food products are maintained in containers. These containers maintain the quantity of the pre-quantified units from the weighing device to the packaging device. Allowing the sanitizing agents to decrease the pathogen quantity of the food product immediately prior to packaging.

By maintaining the identity of discrete pre-quantified units of flowable food products in identifiable containers, a control system can be provided that measures desired properties of each unit of food. In this way, individual bags can be selectively tracked or quarantined based on unit-specific measurements. For example, if a specific unit of the flowable feed did not meet specified moisture level reading, that specific container can be diverted to an alternate path for re-processing or disposal.

By using re-fillable containers, the container itself may be sterilized at a container cleaning station. Separate sanitizing agents may be introduced to the empty container to sterilize or sanitize the container prior to being refilled with subsequent units of the flowable food product.

It is understood that other embodiments will become readily apparent to those skilled in the art from the following detailed description, wherein various embodiments are shown and described by way of illustration only. As will be realized, the concepts are capable of other and different embodiments and their several details are capable of modification in various other respects, all without departing from the spirit and scope of what is claimed as the invention. Accordingly, the drawings and detailed description are to be regarded as illustrative in nature and not as restrictive.

BRIEF DESCRIPTION OF DRAWINGS

Aspects are illustrated by way of example, and not by way of limitation, in the accompanying drawings, wherein:

FIG. 9 is a flow chart showing a method for successively sanitizing pre-quantified units of flowable food products.

FIG. 10 is a flow chart showing a method for successively sanitizing pre-quantified units of flowable food products.

FIG. 11 is a flow chart showing a food sanitizing process.

FIG. 12 is a flow chart showing a process for sanitizing a plurality of units of a flowable food product, pre-measured for packaging.

DESCRIPTION

As noted above, the problem of feed contamination between an initial kill step and the bagging step can be solved by providing a kill step immediately before bagging. The last step in feed processing prior to bagging is generally the weighing or volumetric filler. By inserting a kill step after weighing or volumetric determination, any feed that was contaminated during the feed processing will be safe for consumption when packaged. The term feed means a flowable particulate and can include food for animals or humans. Feed may include beans, rice, pet food, pet treats, pop-corn, candy, or seeds or other similar particulate food items. Particulate food items may be characterized by their flowable nature.

Figure 1:
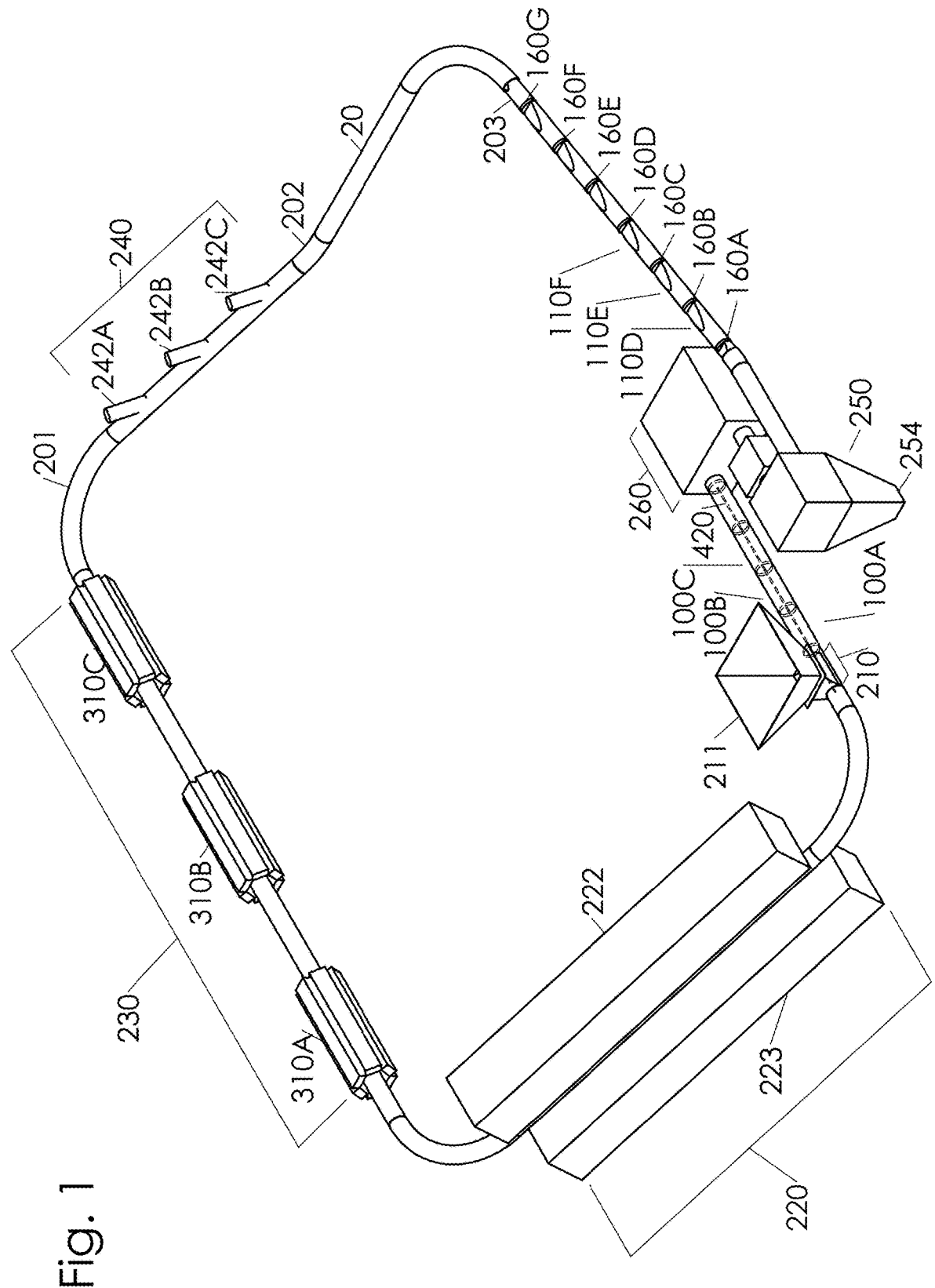
FIG. 1 is a perspective drawing of a sanitizing device having a drag chain conveyor configured to move the containers through the stations.
Figure 2:
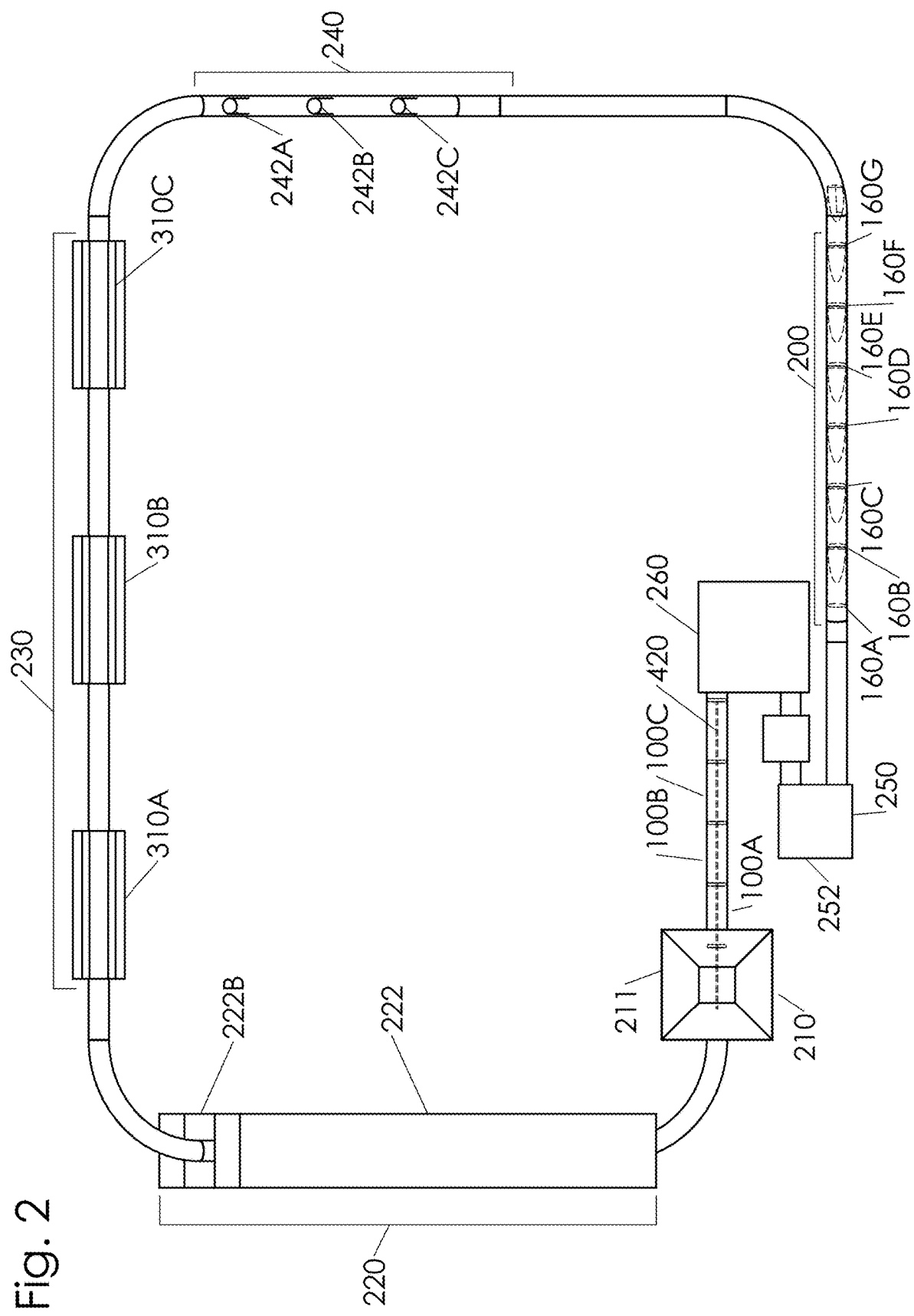
FIG. 2 is a perspective drawing showing a top perspective view of a path of a sanitizing device.

As illustrated in FIG. 1, the sanitizing device receives a unit of the particulate feed into a filling hopper 211. The unit 110 of the particulate animal feed flows into a container 100. The container 100 maintains the unit 110 as a discrete unit ready for bagging, so that the quantity of the unit 110 delivered to the sanitizing device is maintained through the sanitizing process, to be discharged at the dispensing station 250. In this way, the sanitizing device can be seamlessly inserted into the product flow in a feed processing facility, between the measuring station and the bagging station.

As illustrated in FIG. 1, the unit 110 of particulate feed is received into a container 100 at the filling station 210. A plurality of containers 100A, 100B, 100C, 100D, 100E, and 100F are shown in FIG. 1 by rendering a portion of the housing 20 as transparent. The containers 100A, 100B, and 100C are illustrated as empty. The containers 100D, 100E, and 100F are illustrated as filled with a particulate feed. The chain 420 is visible in the empty containers 100A, 100B, and 100C. FIG. 1 shows a drag chain conveyor contained within a housing 20.

In the embodiment illustrated in FIG. 1, the containers are defined by the plurality of plugs 160 and the housing 20. For example, container 100D is defined by a first plug 160A and a second plug 160B and the portion of the housing 20 that is adjacent to the container 100D at the current point of the container's travel along the path 200. The plurality of plugs 160 move with the chain 420. As each container 100 moves through the housing 20, the portion of the housing 20 that is adjacent to the respective container changes. An inlet opening 212 in the housing 20 is positioned at the filling station 210. When one of the plurality of containers 100 is positioned at the filling station 210, the inlet opening 212 allows a unit of the particulate feed to enter the interior open space 150 of that container. The load carried between a pair of plugs is the unit of the flowable product.

The plurality of containers 100 provide a sterile environment with residency time sufficient to expose each unit 110 of the particulate feed to one or more sanitizing agents to pasteurize the pre-quantified unit of the particulate feed. The containers 100 travel along the path 200 to increase the residency time.

The plurality of containers 100 may be made of Teflon. Teflon is an industry accepted sanitary material. Advantages to using Teflon include: good wear resistance, low friction, and does not absorb/hold fats, grease, or chemicals that would promote bacteria growth. In the illustrated embodiment, the plurality of plugs 160 may be made of Teflon. Alternatively, the housing 20 may be made of stainless steel or other food grade material.

Figure 3:
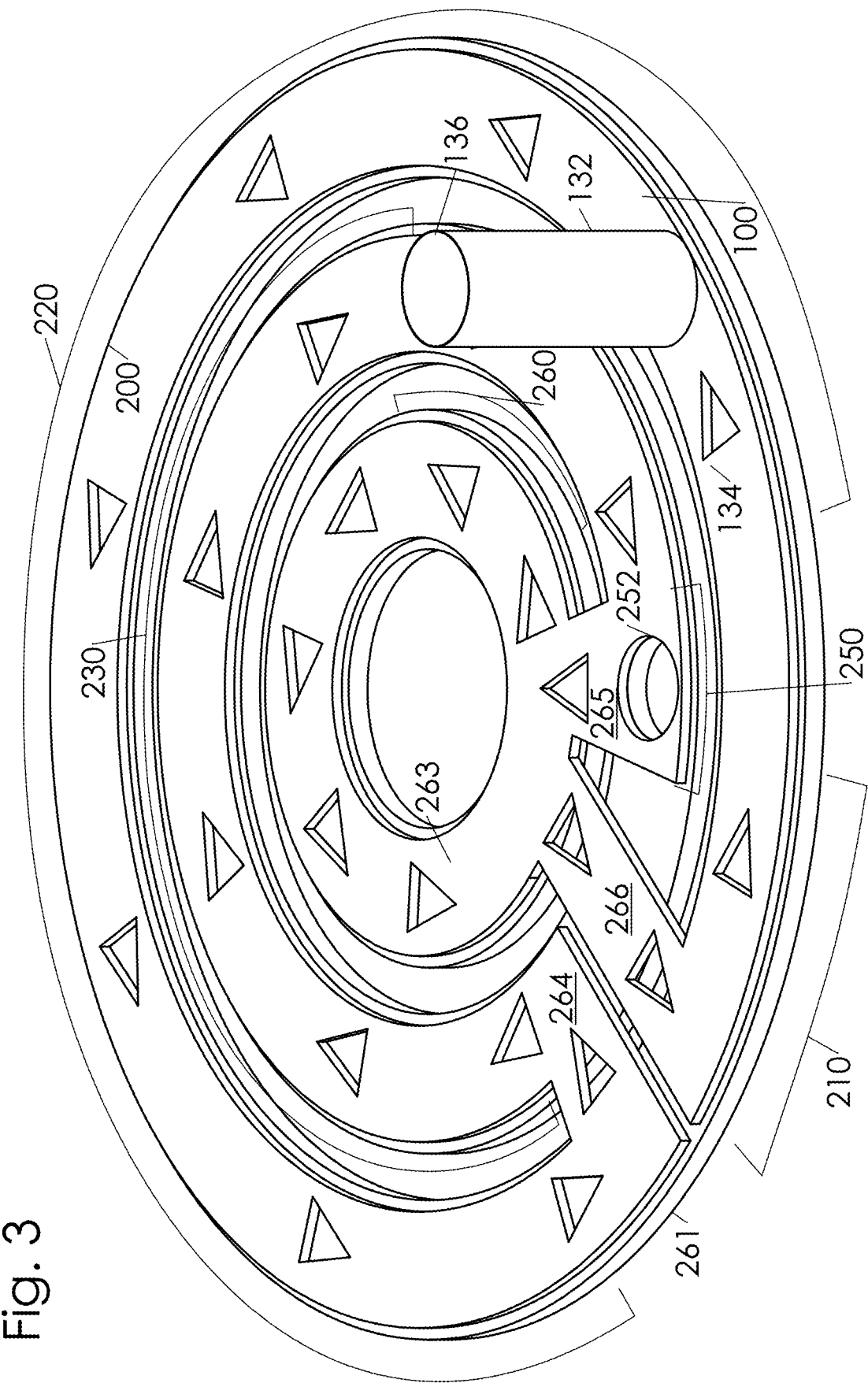
FIG. 3 is a perspective drawing showing a container on a path comprising a plurality of concentric rings interconnected by bridges.

In another embodiment, the containers 100 are vertical cylinders. As shown in FIG. 3, the vertical cylinders have a sidewall 132 that is curved. The vertical cylinders have a hollow center 136 configured to receive the unit 110 of the particulate feed. The vertical cylinders may have a completely or partially open top to allow the particulate feed and the sanitizing agent to enter the containers 100. Similarly, the vertical cylinders may have a completely or partially open bottom to allow the particulate feed to exit the vertical cylinder under the force of gravity. The vertical cylinders can be positioned on top of or adjacent to a conveyor or other drive mechanism.

Additionally, the sidewalls 132 may be perforated to allow a fluid sanitizing agent to enter the containers 100 through the sidewalls. The size of the individual perforations would be smaller than the size of the particulate feed. In another embodiment, the containers have sidewalls 132 that telescope to adjust the volume of the hollow center 136. In this embodiment, the telescoping container has a larger portion and a smaller portion, where the smaller portion is insertable into the larger portion.

In another embodiment, the plurality of containers 100 can comprise shapes other than cylindrical. For example, the shape of the plurality of containers 120 can be conical or rectangular. The shape of the containers 100 can also be at least partially defined by the housing 20. As discussed above, a drag chain conveyor have plugs that correspond to the shape of the housing can define a horizontal cylindrical container.

The containers 100 may be interconnected to one another. An example of interconnected containers is the horizontal cylinders that are connected together with the drag chain. Alternatively, the containers 100 may be independent and not connected to one another. An example of independent containers is a plurality of vertical cylinders that move about the path 200 independent from one another. The vertical cylinders may be interconnected through a framework, and the framework is connected to the drive mechanism. Alternatively, the drive mechanism may individually engage each of the vertical containers.

One advantage to the use of volumetric containers after the quantification step is to maintain the quantity of the pre-quantified unit. The containers 100 prevent any increase or decrease in the quantity of a pre-quantified unit held within the container. Another advantage provided by the containers 100 is an isolated sterile environment for sanitizing the particulate feed. The containers 100, made of a food grade material such as Teflon or stainless steel, can be sterilized when empty. The containers 100 allow the pre-quantified unit of particulate feed to be isolated from further contamination by enclosing the feed unit from the environment of the facility. Another advantage of using containers 100 is to introduce one or more sterilizing agents into the container to effectively reduce any pathogens in or on the particulate feed.

Figure 4:
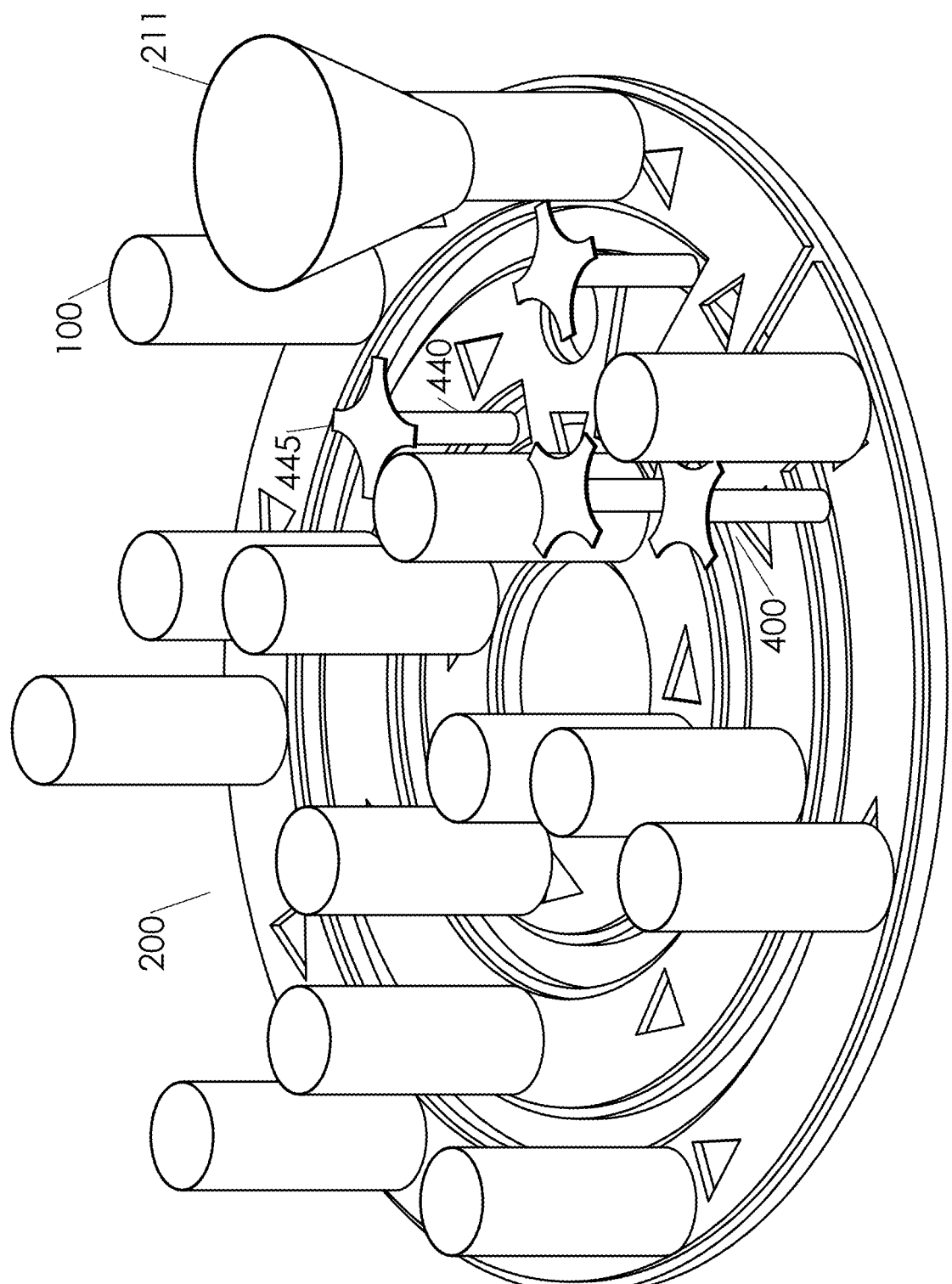
FIG. 4 is a perspective drawing the example of FIG. 3 showing a plurality of containers positioned along a path having a plurality of concentric rings interconnected by bridges and a drive mechanism.
Figure 5:
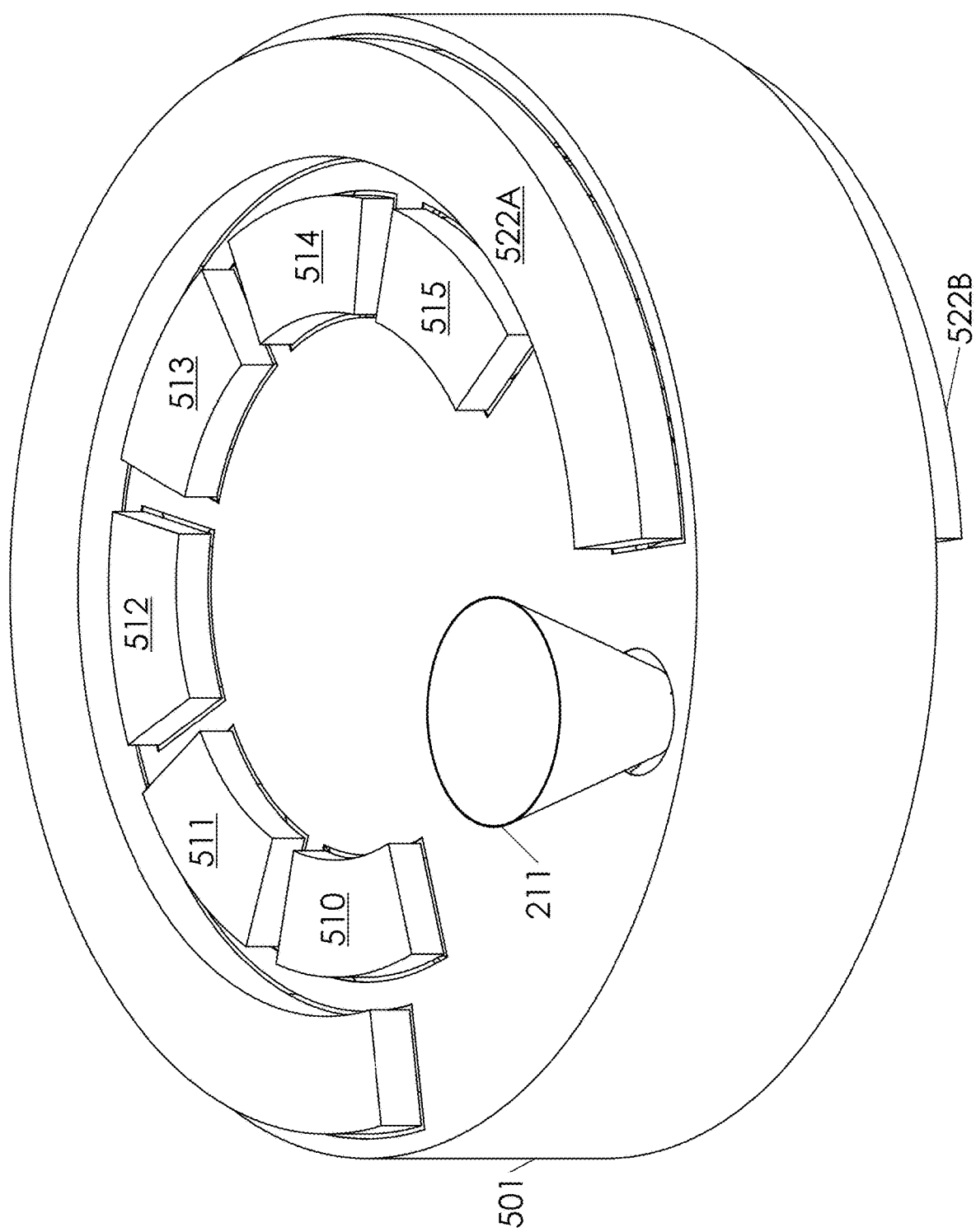
FIG. 5 is a perspective drawing of the example of FIG. 3 showing sanitizing equipment attached to a housing along the path.
Figure 6:
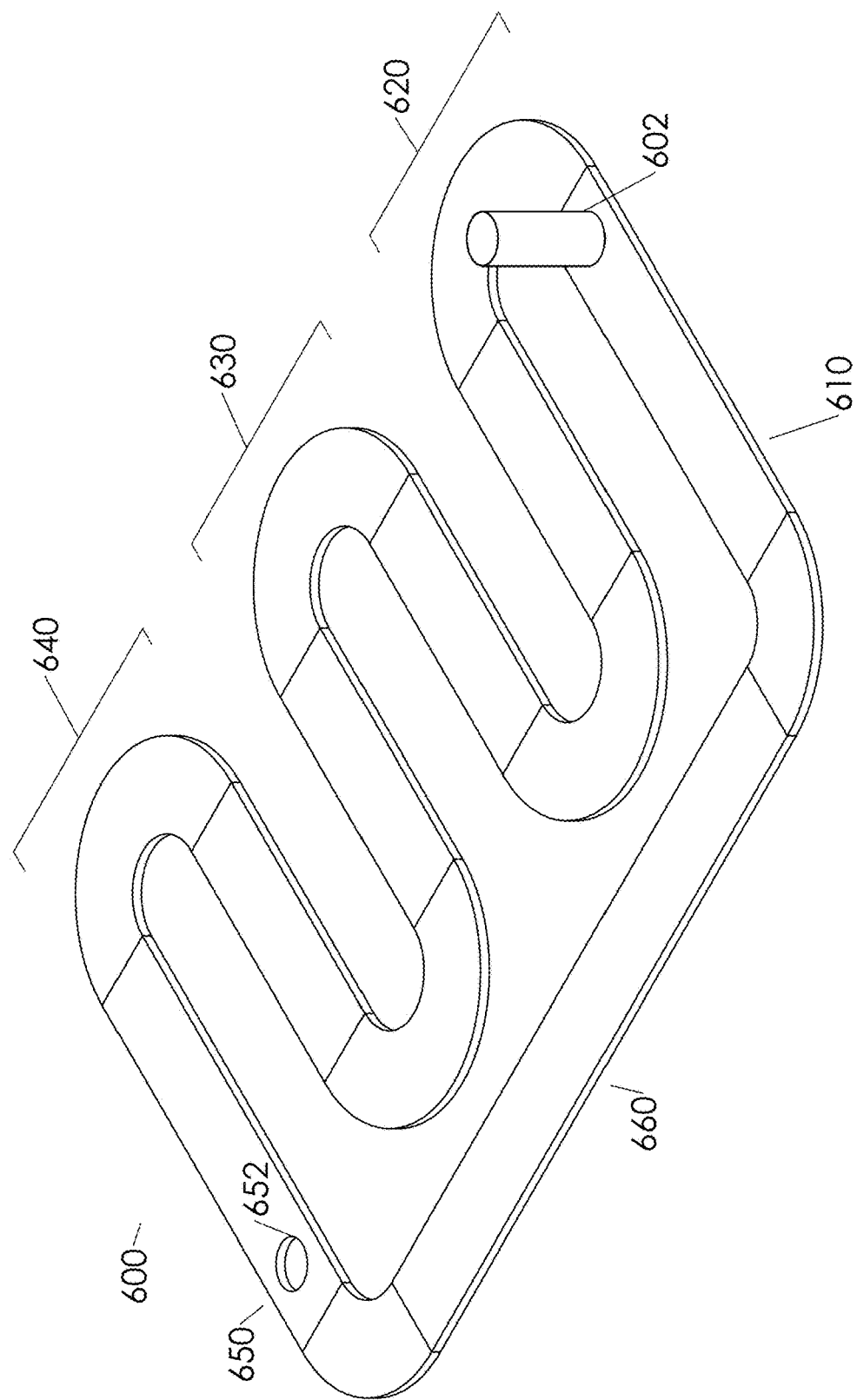
FIG. 6 is a perspective drawing showing a serpentine path having a plurality of stations along which a container may travel.
Figure 7:
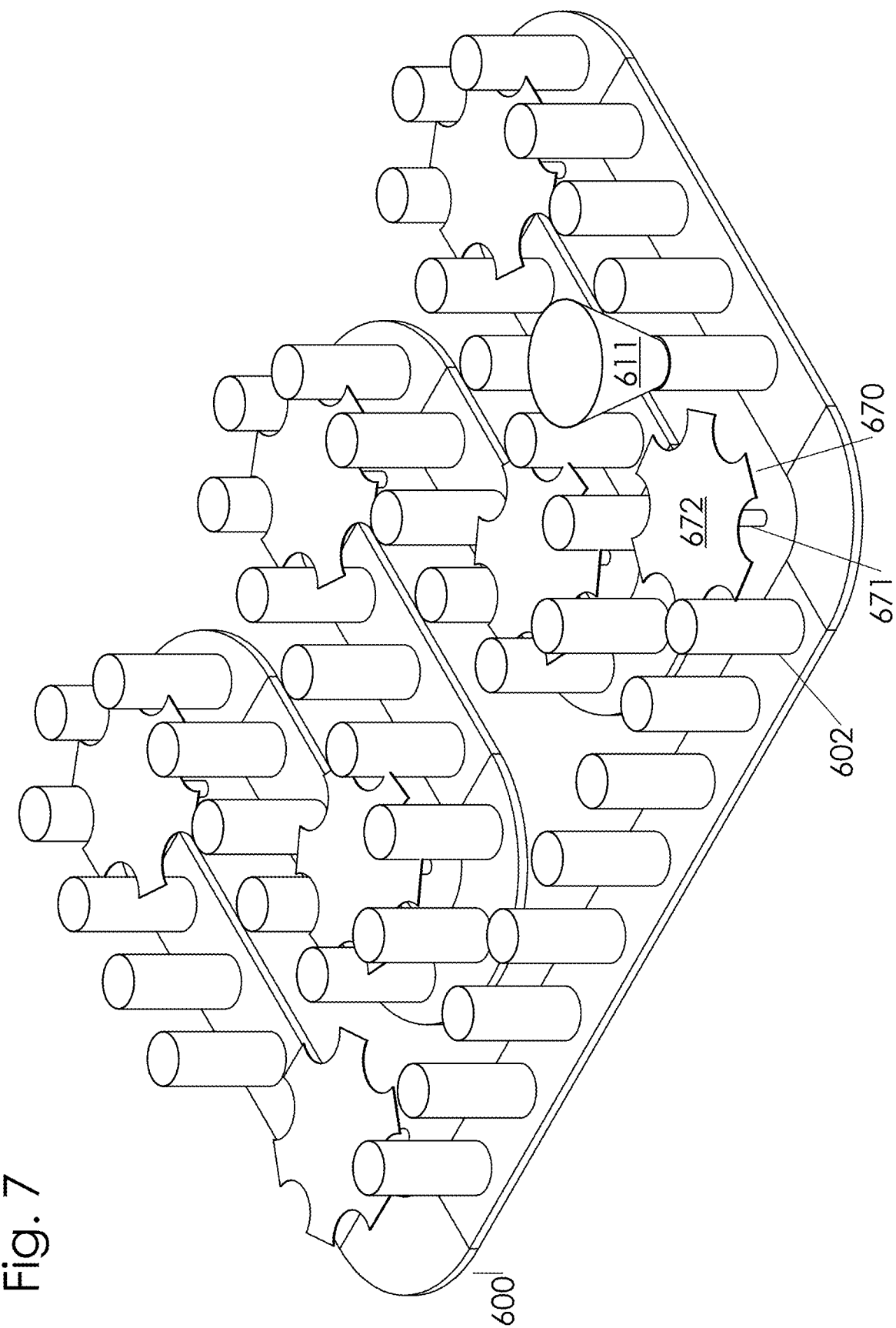
FIG. 7 is a perspective drawing of the embodiment of FIG. 6 showing a plurality of containers positioned along a serpentine path having a plurality of stations along which a container may travel.
Figure 8:
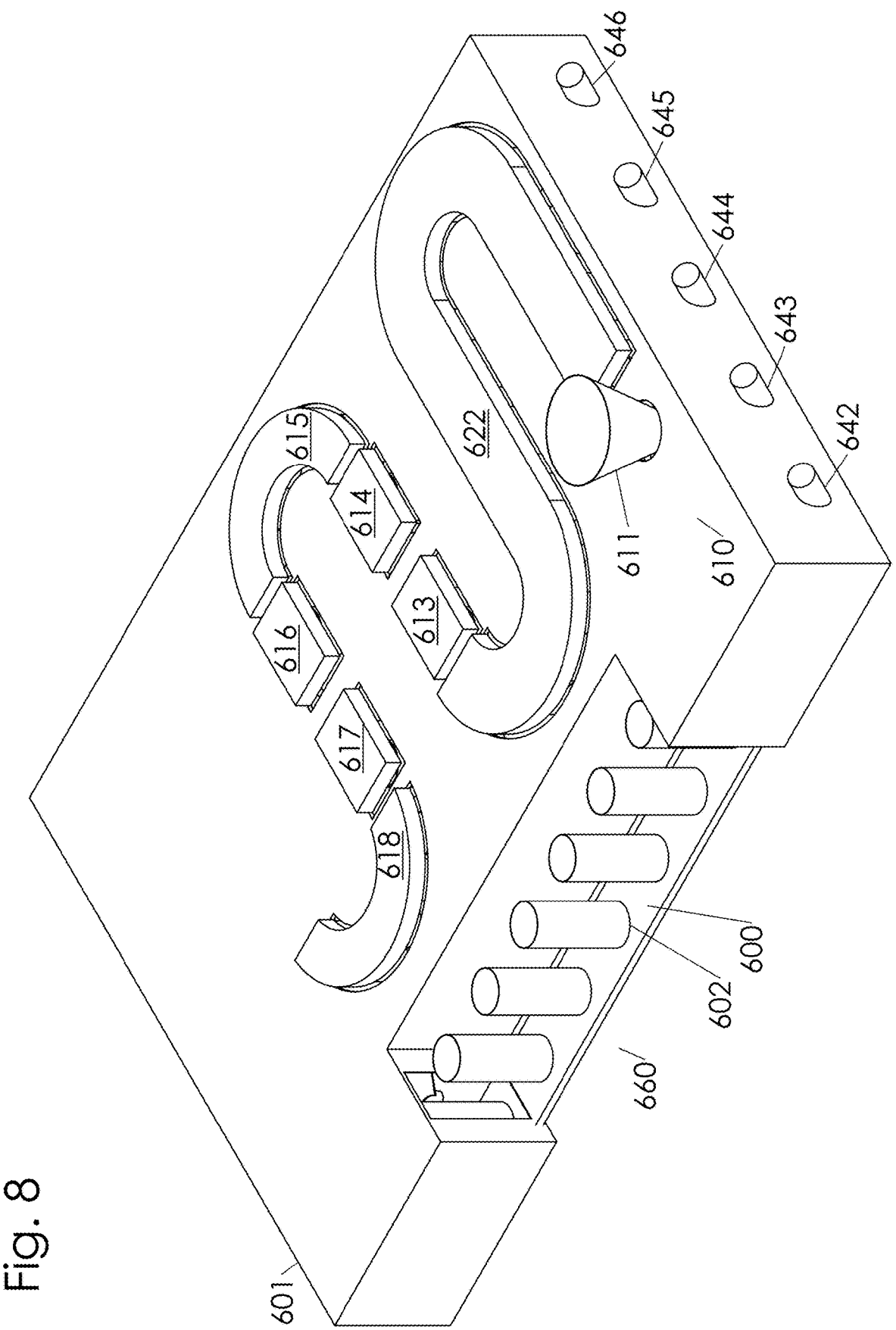
FIG. 8 is a perspective drawing of the embodiment of FIG. 6 showing sanitizing equipment attached to a housing along the path.

As illustrated in FIG. 1, the drive mechanism 400 engages a drag chain conveyor 410 to move the containers 100 about the path 200. It is known in the art to drive a drag chain conveyor 410 using a roller having a sprockets to engage the chain, where the sprocket engage the chain 420 between the plugs 160. Alternatively, and as illustrated in FIG. 4, the drive mechanism 400 comprises sprockets 445 connected to a drive shaft 440. The sprockets are spaced apart to engage each container 100 to push the container along the path. In this way, the drive mechanism is configured to engage individual containers. The drive mechanism 400 may be configured for intermittent movement or continuous movement of the containers 100. The drive mechanism may also be configured to selectively move a particular container along divergent path portions based on a property of the contents of the container. One advantage to using a drag chain conveyor for a drive mechanism is the flexibility of the path links between sanitizing stations such that modular sanitizing stations can be adjustably positioned to accommodate components within an existing facility. Another advantage to using a drag chain conveyor for a drive mechanism is that the narrow design enables access for maintenance within the facility and minimizes obstructions to allow forklifts and other maintenance vehicles to operate in the facility.

In one embodiment, the sanitizing device comprises one or more detection devices to determine a property of the contents of the container. The detection device may generate one or more signals corresponding to detected properties of the contents of the container. For example, the detection device could be a scale to determine the weight of the contents of the container, a thermometer to determine the temperature of the contents of the container, or a near-infrared reflectance spectroscopy device for determining food quality. The detection device could be selected from those devices known in the industry to determine the moisture content, density, fat content, protein content, amino acid content, oil content, carbohydrate content, allergens, color, pallitant content, ash content, total minerals content, selected minerals content, total vitamin content, or selected vitamin content. The detection device may be configured to measure the contents within the container or a sample may be removed from the container. A control system is configured to associate the measured property or properties of a particular container. The control system can be configured to compare the measured property with a standard control value. If the measured value of the contents of a particular container do not conform with the desired range of the property, then the contents of that container can be diverted to a separate path, rather than discharging the contents of that container into the bagging device. By tracking specific units of product within specific containers, the control system can confirm appropriate product characteristics with measurements specific for individual packages.

The drive mechanism 400 may also be configured to time the movement of the containers with the discharge of the upstream weighing device. For example, a combination scale upstream of the sanitizing device may dispense up to one hundred pre-quantified units at a given weight per minute. The drive mechanism 400 is configured to synchronize the movement of the plurality of containers 100 such that an empty container is positioned below the scale to receive each of the dispensed pre-quantified units. In this embodiment, the drive mechanism 400 is configured to move up to one hundred containers 100 through the filling station in one minute.

The drive mechanism 400 may also be configured to time the movement of the containers with the bagging device downstream of the sanitizing device. For example, the bagging device may be configured to bag at up to fifty bags per minute. The drive mechanism 400 may be configured to match the dispensing rate to the bagging device such that up to fifty containers 100 pass through the dispensing station 250 every minute. Alternatively, the path may be configured for a first dispensing station at a first bagging device and a second dispensing station at a second bagging device. In order to facilitate delivery to multiple bagging devices, the path may diverge such that a first subset of the containers are directed to the first dispensing station located on a first sub-path and a second subset of containers are directed to the second dispensing station located on a second sub-path. Alternatively, the first dispensing station may be inline on the same path as the second dispensing station. In this configuration, the first dispensing station has a first discharge aperture that is selectively open to allow the particulate from a first subset of containers to dispense at the first dispensing station. And the second dispensing station has a second discharge aperture that is selectively open to allow the particulate from a second subset of the containers to dispense at the second dispensing station.

In another embodiment, the drive mechanism 400 may comprise a conveyor belt that directly engages the containers. The conveyor belt can be to a horizontal side of the container, above the container, or below the container. In one embodiment, the conveyor belt works in cooperation with a rotating star turret, as shown in FIG. 4.

As illustrated in FIG. 1, the path 200 comprises a circuit with the dispensing station 250 adjacent to the filling station 210. The path 200 incorporates an angle section 201, an incline section 202, and a clear sight section 203. The angle section 201 displayed in FIG. 1 is a 90° angle section, however the angle section can comprise a different angle in order to accommodate different paths requirements. For example, in order to accommodate a specific facility setup, the path 200 may incorporate multiple twists and turns.

The path may also incorporate an incline section 202, as shown in FIG. 1. A path 200 comprising the incline section 202 may provide an advantage by allowing the dispensing station 250 to be located at the same height as the filling station 210. In this way, the scale device does not have to be raised to accommodate the presence of the sanitizing device. There is often minimum extra head height available at a facility, and the lateral movement of equipment is much easier and less expensive to facilitate compared with lifting equipment vertically higher. Additionally, incorporating an incline section 202 or a decline section (not shown) causes the particulate feed to shift within the container 100. Moving the particulate feed within the container 100 causes different surface areas of the particulate feed to be exposed. Some sanitizing agents, such as ozone, are more effective when directly exposed to the surface of the particulate animal feed. The vertical movement of the containers may increase the efficacy of such sanitizing agent.

In one embodiment, the path comprises multiple concentric rings, as shown in FIG. 3. The arrows of FIG. 3 indicate the direction of flow of the containers as the receptacle follows the path 200. The containers may be filled on the outer ring at the filling station 210. The filling hopper 211 receives the pre-quantified unit of feed from the scale and acts as a transition piece to guide the unit through the inlet opening 212 and into the container 100. While still in the outer ring 261, the container enters a first sanitizing station 220 where a first sanitizing agent, such as radio frequency, is applied to the pre-quantified unit in the container 100. In this way, the sanitizing occurs immediately upon introduction to the receptacle and the retention time in a sanitizing condition is increased. The container 100 follows the path 200 over a first bridge 264 to enter the middle ring 262. Transfer of the container from the outer ring 261 to the middle ring 262 can be accomplished with a driven wheel having a plurality of sprockets that direct the container from the outer ring to the middle ring. The middle ring 262 comprises a second sanitizing station 230 where a second sanitizing agent can be introduced. For example, receptacle containing the measured quantity of product can be exposed to Ozone by flooding ozone into the second sanitizing station 230 with ozone injection portions disposed about the middle ring 262. The ozone may be pre-chilled to cool the particulate animal feed after being heated by the first sanitizing agent of the first sanitizing station. Alternatively, the ozone may be introduced at room temperature, which may also facilitate the cooling process to remove any heat introduced during an earlier sanitizing step. The ozone may be introduced as a liquid or as a gas. These containers would dispense through the discharge aperture 252 at the dispensing station 250 under the force of gravity and into the product bagging device located below the sanitizing device. The empty containers cross the second bridge 265 to enter the inner ring 263 for sanitation of the container 100 at the container cleansing station 260. Once the container is cleaned, the container crosses the third bridge back out to the outer ring 261 for subsequent filling and sanitizing cycles. In one embodiment, the path comprises a plurality of concentric path portions, where the outer path portions at least partially surround one or more inner path portions. The containers may move about the concentric path portions in a contra-rotating manner, such that the container moves clockwise in a first path portion and counterclockwise in a second path portion. For example, in FIG. 3 the arrows indicate the direction of container movement, the movement of the containers in the center path portion is shown as clockwise and the movement of the containers in the innermost and outermost path portions is shown as counterclockwise. It is also contemplated that the bridge members and drive mechanism can be configured to facilitate co-rotation, where the containers move along each path portion in generally the same direction.

In another embodiment, the path 200 comprises a curvilinear route, an example of which is shown in FIG. 4. The containers 100 travel along the path 200 through a plurality of stations. The path 200 is curvilinear and circuitous in order to increase retention time of the particulate feed in the container to increase the exposure to the various sanitizing agents at the sanitizing stations. The path comprises a filling station 210, a first sanitizing station 220, a second sanitizing station 230, a third sanitizing station 240, a dispensing station 250, and a container cleaning station 260. In one embodiment, a driven wheel having a plurality of sprockets can be disposed at each of the curves to propel the containers 100 along the path 200. In another embodiment, a linear conveyor belt having a plurality of cleat members extending from the belt is disposed along the linear portions of the path 200 to propel the containers 100. FIG. 5 depicts the embodiment shown in FIG. 4 with an external housing 501 intact. An RF transmitter is mounted to the external housing 501 along the path 200 at the first sanitizing station 220. The RF transmitter comprises a first electrode 522 mounted to a top portion of the external housing 501 and a second electrode 523 mounted to a bottom portion of the external housing 501. The first electrode 522 is mounted parallel to the second electrode 523. An RF power oscillator is connected to the parallel electrodes (not shown) to generate the desired frequency and power of radio frequencies. A plurality of UV light sources 510, 511, 512, 513, 514, and 515 are shown mounted to a top portion of the external housing 501 along the path above the second sanitizing station 230.

FIG. 6 depicts a path 600 that is serpentine and has a plurality of stations along which a container may travel, such as a filling station 610, a first sanitizing station 620, a second sanitizing station 630, a third sanitizing station 640, a discharge station 650 with a discharge aperture 652, and a container cleaning station 660. As shown in FIG. 7, a drive mechanism 670 comprises sprockets 672 connected to a drive shaft 671. The sprockets 672 are spaced apart to engage each container 602 to push the container along the path 600. In this way, the drive mechanism is configured to engage individual containers. The drive mechanism 670 may be configured for intermittent movement or continuous movement of the containers 602. The drive mechanism may also be configured to selectively move a particular container along divergent path portions based on a property of the contents of the container. As illustrated in FIG. 8, path 600 may be partially enclosed by an external housing 601. The external housing 601 confines the sanitizing agents and may prevent external contamination from entering the containers 602. The first sanitizing station 620 is equipped with a plurality of inlet ports 642, 643, 644, 645, and 646 which can be connected to an ozone supply to introduce ozone gas into the external housing 601. One or more ports allow ozone gas to be flooded into the housing and enter the containers passing through the first sanitizing station 620. A UV light source 613, 614, 615, 616, 617, 618 mounted to a top portion of the external housing 601 and along the path 600 through the second sanitizing station 630. The UV light source 613, 614, 615, 616, 617, 618 extends along the path 600 to expose the particulate feed within the container 602 to the UV radiation. An RF transmitter is mounted to the external housing 601 along the path 600 at the first sanitizing station 620. The RF transmitter comprises a first electrode 622 mounted to a top portion of the external housing and a second electrode (not shown) mounted to a bottom portion of the external housing. The first electrode 622 is mounted parallel to the second electrode. An RF power oscillator is connected to the parallel electrodes (not shown) to generate the desired frequency and power of radio frequencies. The filling station 610 comprise a filling hopper 611 and an inlet aperture in the top portion of the external housing 601.

In another embodiment, the first sanitizing station 220 overlaps with the second sanitizing station 230. For example, the first sanitizing station 220 exposes the particulate feed to UV light. The second sanitizing station 230 exposes the particulate feed to Ozone gas. The portion of the path of the first sanitizing station 220 may completely or partially overlap the second sanitizing station 230 such that in a portion of the path the container filled with the particulate feed is exposed to both sanitizing agents.

In one embodiment, a vibratory feed tray is incorporated along the path to spread the particulate feed out to single layer depth. The vibratory feed tray can be disposed at the filling station 210 or at a sanitizing station. An advantage to incorporating a vibratory feed tray is that some sanitizing agents, such as UV and RF, are more effective with direct contact with the exterior surface of the particulate feed.

As illustrated in FIG. 1, one of the sanitizing stations may comprise an ultraviolet (UV) light source configured to transmit a sanitizing dose of UV radiation. In one embodiment, the UV light source emits UV light having a wavelength between 100 to 400 nanometers. In another embodiment, the UV light source emits UV germicidal irradiation (UVGI), short wavelength UV-C with wavelengths of 200 nm-280 nm. In another embodiment, the UV light source emits UV light having wavelengths of 250-270 nm. The UV treatment is quantified by the UV dose, where UV Dose is equal to UV Intensity (I) multiplied by the Exposure Time (t). The UV intensity (I) is determined by the equipment selected. The UV Dose will be determined by the length of the UV light source and the intensity of the UV light in order to provide a sanitizing affect on the particulate feed. The UV Dose may also be determined according to the type of particulate feed, including the moisture content.

The UV light source 310 may comprise a UV Low-Pressure lamp, a UV Medium-Pressure Lamps, or a UV amalgam Lamps such as those lamps that are commercially available from Heraeus Noblelight, LightTech and LightSources. In one embodiment, the UV lamp is disposed within the housing. The UV lamp extends along the path to expose the particulate feed to the UV radiation. In one embodiment, the UV lamp is inserted into the container containing the particulate feed. The UV lamp may travel with the container. Alternatively, for use with an intermittent drive mechanism, the UV lamp may be inserted into a momentarily stationary container.

The UV lamps may be surrounded by a quartz sleeve to prevent a lamp from being directly exposed to the feed and to protect the lamp from air and water flow, breakage, leakage, temperature fluctuations, and environmental hazards. As UV lamp effectiveness is decreased when covered in dust or debris, the sanitizing device may include means for cleaning the lamp or sleeve cleaning. This lamp or sleeve cleaning means could comprise a manual cleaning process or an automated cleaning mechanism for removing the dust from the lamp.

In another embodiment, the UV lamp operates in a low dust environment. For example, the housing may incorporate sight glass provided by Fresco Systems Pty Ltd. Direct at the sanitizing station that utilizes UV light. The sight glass provides translucent in-line polycarbonate conveying tube providing up to a 360° full-view window through which UV light may be transmitted without risk of dust accumulating on the lamp. Incorporating sight glass into portions of the housing also allows the operator to observe material flow in pneumatic conveying lines. In another embodiments, the container sidewalls incorporate sidewalls that allow the applicable UV radiation to pass through. Examples of suitable materials include plastics which are suitable for use with food, such as cyclic olefin copolymer (COC) or Fluorinated Ethylene Propylene (FEP). Alternatively, the suitable housing material for use with a UV sanitizing station may include a glass or a glass wrapped in a food safe plastic.

In one embodiment, the environment within the housing is maintained at less than or equal to 70% relative humidity to increase UV efficacy. The environment may be maintained by introducing conditioned air into the housing, operating a dehumidifier, or other means known in the industry. In another embodiment, the UV lamp is maintained at operating temperature ranges between 77° F.-80° F. to increase efficacy of the UV transmission.

In order to increase the amount of surface area of the particulate feed that is exposed to the UV light, the particulate feed may be moved within the container. UV light is effective at sanitizing surfaces. The particulate feed may stack upon itself in the container in such a way that portions of the particulate feed are hidden by other portions of feed, which may reduce the efficacy of the UV light. Additionally, the stacking of one particulate feed piece upon a second particulate feed piece may prevent that contact area from being sanitized by the UV radiation by blocking sightlines. The container may be vibrated to rearrange the particulate feed within the container, changing the orientation and stacking of particulate feed to increase surface area exposed to the UV radiation. Alternatively, the path may incorporate features that cause the particulate feed to be rearranged within the container. For example, the path may incorporate rising sections and falling sections to cause the feed to shift position within the container while maintaining the quantity of the pre-quantified unit within the container. Alternatively, the path may incorporate ridges that vibrate the feed within the container as the container passes over the ridges. Alternatively, the UV light source may be inserted into the container at one or more sanitizing stations along the path. Alternatively, the UV light source can be embedded in the containers, such as by surrounding the lamps with Teflon, polycarbonate, plastic, or FEP to prevent breakage.

UV radiation may be effective at sanitizing the surface of the particulate feed. This may be advantageous, as the initial kill step in a feed processing facility, such as by extrusion, can effectively sanitize the product. As the particulate feed is processed in the facility, the exterior surface of the particulate feed may come into contact with pathogenic material—either through equipment contamination or contamination from a worker. In either case, the pathogenic material is likely applied to the exterior surface of the particulate feed. The UV radiation is effective at treating this type of exterior surface contamination.

As illustrated in FIG. 1, the first sanitizing station 220 includes a radio frequency (RF) transmitter. The RF transmitter generates RF wavelengths at a given frequency to sanitize the particulate feed in the containers passing through the first sanitizing station 220. The nonionizing electromagnetic radiation is applied to the particulate feed to produce heat and sanitize the feed. The RF transmitter is displayed in FIG. 1 as first electrode 222 and a second electrode 223, where the first electrode is parallel to the second electrode. An RF power oscillator is connected to the parallel electrodes to generate the desired frequency and power of radio frequencies.

The RF frequency and power specifications will be determined based on the product to be treated. In one example, Radio Frequency, Inc. has shown that RF having 30 kW of output power at an operating frequency of 40 MHz is sufficient to achieve a greater than 6 log reduction in almonds for the pathogen SE PT30, which is particularly resistant to dry heat treatment.

The RF transmitter may emit longer wavelength, or lower frequency, to increase penetration and decreases heating time. Lower frequency RF increases penetration into the feed and may heat more uniformly through the material. In one embodiment, the RF transmitter emits at a frequency of between 10 MHz to 50 MHz, in one embodiment the RF is generated at 13.56 MHz, 27.12 MHz, or 40.68 MHz, frequencies approved by the FDA.

The electrode may be placed above and below the container, or on either horizontal side as the container travels the path. The wavelength, shape, power, distance, and path length of the RF transmitter may be configured depending on the type of product being sanitized. In one embodiment, the temperature of the surface of the particulate feed is raised to 194° F. by the RF. In one embodiment of the method, the sanitized feed product is dispensed at an elevated temperature into the bagging station. The feed may be hot stacked to increase the pasteurization time. Alternatively, the sanitizing device may incorporate a cooling station wherein the particulate feed is rapidly cooled within the container 100. In one embodiment, a cooling agent is introduced into the sanitizing device. This cooling agent may also be a sanitizing agent. For example, ozone may be introduced at or below the ambient temperature and act as both a cooling agent and a sanitizing agent.

Incorporating an RF transmitter at a sanitizing station is advantageous for quickly heating the surface of the feed particulate. Rapid heating is beneficial, as strains of salmonella can become resistant to heat damage when the temperature rises slowly. The RF transmitter increases the temperature of the feed product rapidly, reducing the opportunity for a pathogen to develop resistance. Sanitizing with RF also offers the advantage of being more consumer-friendly, as RF is a dielectric process and not ionizing.

The RF sanitizing station may overlap with the UV sanitizing station on the path, such that the container is simultaneously exposed to RF treatment and UV radiation.

As illustrated in FIF. 1, the third sanitizing station 240 is equipped with a plurality of inlet ports 242A, 242B, 242C which can be connected to an ozone supply to introduce ozone gas into housing 20. One or more ports allow ozone gas to be flooded into the housing and enter the containers passing through the third sanitizing station. Ozone gas is effective as a pasteurizing agent. In one embodiment, Ozone gas is maintained in the sanitizing station at between 3 part per million (ppm) to 8 ppm. In one embodiment, the ports are connected to a source of aqueous ozone. The aqueous ozone may be applied with spray nozzles. For example spraying aqueous ozone at 2.7 ppm may be effective in eliminating E. Coli.

In one embodiment, containers have a porous wall to facilitate the introduction of a fluid sanitizing agent—such as aqueous or gaseous ozone—into the container. The ozone can be introduced under sufficient pressure to lift and move the particulate feed within the container. In this way, more of the surface area of the particulate feed is exposed to the ozone. It may be advantageous to maintain the ozone sanitizing station separate from the UV sanitizing station, to prevent the Ozone from reducing the efficacy of the UV radiation.

In another embodiment, a sanitation station may include an applicator for a fluid sanitizing agent such as Ethylene Oxide (EtO) or Propylene Oxide (PPO). The embodiment may comprise applicators—such as spray nozzles or atomizer heads—that are fluidly connected to a pressurized source of the fluid sanitizing agent. The fluid sanitizing agent may be introduced at a temperature less than ambient temperature to assist in cooling the particulate feed after a heat pasteurization step, such as the RF sanitizing station.

In another embodiment, a sanitizing station comprises gamma radiation or e-beam radiation for pathogenic microorganism control. For gamma irradiation, the does may range from between 5 to 50 kiloGrays (kGy), in another embodiment the gamma irradiation dose ranges from 20 to 25 kGy, in another embodiment the gamma irradiation dose ranges from 25 to 35, in another embodiment the gamma irradiation dose ranges from 35 to 45 kGy.

In existing facilities, the material is quantified, such as by weight, count, or volume, and then discharged into a bagging device—either directly or indirectly. In order to provide a pasteurization or sanitation step immediately prior to bagging, the sanitizing device receives the pre-quantified unit of particulate feed that would otherwise be received into the bagging device. The sanitizing device maintains the quantity of the pre-quantified unit with the container 100. The pre-quantified unit is maintained as a discrete unit throughout the pasteurizing process at the various sanitizing stations. The pre-quantified unit is dispensed at the dispensing station 250 into the bagging device after the passing through the various sanitizing stations. The container is then sterilized at the container cleaning station 260. The empty and clean container returns to the filling station 210 to be refilled with another pre-quantified unit of the particulate feed.

The particulate feed can be quantified using any standard quantification device appropriate for the feed selected. For example, combination net weighers are commonly used for weighing or counting a wide range of products including confectionary, bakery, pet food, pet treats, pasta, cereal, fresh produce, and snack foods. Combination weighers can deliver up to one hundred discharges per minute to the sanitizing device. Examples of a material fill source can a combination scale, such as a 10-Head, 14-Head, or 20-Head Combination Scale from Parsons-Eagle. Alternatively, the material fill source can comprise a linear scale, such as a Parsons-Eagle LS, E, HE, or NW Series Linear Scale. Alternatively, a volumetric filler may be used.

The dispensing station may discharge into a packaging device, such as a bagging system. As discussed above, the sanitizing device maintains the quantity of a pre-quantified unit of feed. Once the container reaches the dispensing station 250, the contents of the container are discharged under the flow of gravity. In one embodiment, the unit flows under the force of gravity directly to a bagging system, such as Thiele's UltraStar bagging system. The timing of the discharge and bagging is synchronized between the bagging system and the rate of flow of container arriving at the dispensing station.

At the container cleaning station, the container 100 is cleaned to prepare to receive the next pre-quantified unit of particulate feed. The cleaning may comprise a sterilization procedure, such as spraying a mist to prevent the build up or coating on the hollow center 136 of the empty containers. The container cleaning station may include the step of spraying Acidified Calcium Sulfate (ACS), Ethylene Oxide (EtO), Propylene Oxide (PPO) onto the container 100. The empty container may be exposed to UV radiation to sterilize the container itself. The empty container may be heated to a sufficient temperature to sterilize the container. The empty container may be subject to irradiation. The empty container may be subject to steam sterilization.

General Sterilization Procedure: Without Sterilization when Empty.

a. Step 1: A predetermined amount of a product enters a self-contained section of the device along the path. This entry point along the path is called the inlet.

b. Step 2: The self-contained section moves along the path to Decontamination Region 1. The product inside the section is exposed to one or more sterilization methods. The distance along the path that Decontamination Region 1 encompasses is determined by the residence time required to achieve the desired level of decontamination.
c. Step 3: The self contained section proceeds along the path, exiting Decontamination Region 1 and entering Decontamination Region 2. The product inside the container is again exposed to one or more sterilization methods. These methods can be the same or different from those used in Step 2. The distance along the path that Decontamination Region 2 encompasses is determined by the residence time required to achieve the desired level of decontamination.
d. Step 4: The self-contained section with predetermined amount of product continues along the path passing through X number of Decontamination Regions until the desired level of sterilization is reached. The distance along the path that Decontamination Region X encompasses is determined by the residence time required to achieve the desired level of decontamination.
e. Step 5: When the product passes through X number of Decontamination Regions the self-contained section continues to move along the path and the predetermined amount of product exits the self-contained section of the device. This exit point along the path is called the discharge.
f. Step 6: The self-contained section of the device, now empty, returns to the inlet at step 1.
g. Steps 1-6 repeat until the desired amount of product is processed.

General Sterilization Procedure: With Sterilization when Empty
a. Step 1: Predetermined amounts of a product enter a self-contained section of the device along the path. This entry point along the path is called the inlet.
b. Step 2: The self-contained section moves along the path to Decontamination Region 1. The product inside the section is exposed to one or more sterilization methods. The distance along the path that Decontamination Region 1 encompasses is determined by the residence time required to achieve the desired level of decontamination.
c. Step 3: The self contained section proceeds along the path, exiting Decontamination Region 1 and entering Decontamination Region 2. The product inside the container is again exposed to one or more sterilization methods. These methods can be the same or different from those used in Step 2. The distance along the path that Decontamination Region 2 encompasses is determined by the residence time required to achieve the desired level of decontamination.
d. Step 4: The self-contained section with predetermined amount of product continues along the path passing through X number of Decontamination Regions until the desired level of sterilization is reached. The distance along the path that Decontamination Region 2 encompasses is determined by the residence time required to achieve the desired level of decontamination.
e. Step 5: When the product passes through X number of Decontamination Regions the self-contained section continues to move along the path and the predetermined amount of product exits the self-contained section of the device.
f. Step 6: The self-contained section of the device, now empty, passes through Cleaning Region A, where one or more sterilization methods is applied to the self-contained section of the device. This exit point along the path is called the discharge.
g. Step 7: The self-contained section of the device, now empty and sterilized, returns to the inlet at step 1.
h. Steps 1-7 repeat until the desired amount of product is processed.

One specific sterilization procedure example includes the steps as follows:
a. Step 1: Predetermined amounts of a product enter a self-contained section of the device along the path. This entry point along the path is called the inlet.
b. Step 2: The self-contained section moves along the path to Decontamination Region 1. The product inside the self-contained section is exposed to Radio Frequency at 40.68 MHz. The distance along the path that Decontamination Region 1 encompasses is determined by the residence time required to achieve the desired level of decontamination.
c. Step 3: The self contained section proceeds along the path, exiting Decontamination Region 1 and entering Decontamination Region 2. The product inside the self-contained section is exposed UV type C light with wavelength of 250-270 nm. The distance along the path that Decontamination Region 2 encompasses is determined by the residence time required to achieve the desired level of decontamination.
d. Step 4: The self contained section proceeds along the path, exiting Decontamination Region 2 and entering Decontamination Region 3. The product inside the self-contained section is exposed to ozone gas. The distance along the path that Decontamination Region 3 encompasses is determined by the residence time required to achieve the desired level of decontamination.
e. Step 5: When the product passes through Decontamination Region 3 the self-contained section continues to move along the path and the predetermined amount of product exits the self contained section of the device. This point exit along the path is called the discharge.
f. Step 6: The self-contained section of the device, now empty, passes through Cleaning Region 1, where one or more sterilization methods are applied to the self-contained section.
g. Step 7: The self-contained section of the device, now empty and sterilized, returns to the inlet at step 1.
h. Steps 1-7 repeat until the desired amount of product is processed.

One general aspect includes an automated pasteurization system configured to perform particular operations or actions by virtue of having software, firmware, hardware, or a combination of them installed on the system that in operation causes or cause the system to perform the following actions. One or more computer programs can be configured to perform particular operations or actions by virtue of including instructions that, when executed by data processing apparatus, cause the apparatus to perform the actions. One general aspect includes a continuous food pasteurizing process, the steps of the process including: receiving a first unit of a particulate animal feed directly into a first container at a filling station, the first unit being discrete and pre-measured; moving the first unit in the first container along a path; exposing the first unit to a first sanitizing agent at a first sanitizing station disposed along the path; dispensing the first unit from the first container for subsequent packaging at a dispensing station disposed along the path; and returning the first container to the filling station for refilling with a second unit of the particulate animal feed. Other embodiments of this aspect include corresponding computer systems, apparatus, and computer programs recorded on one or more computer storage devices, each configured to perform the actions of the methods.

Implementations may include one or more of the following features. The process further including: exposing the first container to a discharge aperture dispense the first unit of the particulate animal feed under the force of gravity. The process further including the steps of: flooding the first container with a fluid sanitizing agent at a second sanitizing station disposed along the path. The process further including the steps of: admitting the fluid sanitizing agent into the first container through a plurality of perforations in a wall of the first container. The process where the fluid sanitizing agent includes ozone gas. The process further including the step of: providing an ultraviolet light source to generate an ultraviolet radiation as the first sanitizing agent. The process further including the step of: admitting the ultraviolet radiation into the first container through a wall of the first container. The process further including the step of: positioning the first container at the filling station prior to the step of receiving the first unit of the particulate animal feed, where the first container includes an open space between a first plug and a second plug of a drag chain conveyor. Implementations of the described techniques may include hardware, a method or process, or computer software on a computer-accessible medium.

One general aspect includes a sanitizing device for sanitizing a quantified unit of a free flowing particulate feed, the sanitizing device including: a housing having an inlet opening and a discharge opening; a plurality of containers disposed within the housing; a driven mechanism operably connected to the plurality of containers to move the plurality of containers along a path; a receiving station disposed along the path, the receiving station configured to receive the quantified unit of the free flowing particulate feed into a first container of the plurality of containers through the inlet opening in the housing; a dispensing station disposed along the path, the dispensing station configured to dispense the quantified unit of the free flowing particulate feed through the discharge opening in the housing; a first sanitation station disposed along the path between the receiving station and the dispensing station; and where the plurality of containers are configured to contain the. Other embodiments of this aspect include corresponding computer systems, apparatus, and computer programs recorded on one or more computer storage devices, each configured to perform the actions of the methods.

Implementations may include one or more of the following features. The sanitizing device where each of the plurality of containers includes a cylindrical shape. The sanitizing device where each of the plurality of containers has a sidewall that is perforated. The sanitizing device where the plurality of containers include a sidewall defined by the housing. The sanitizing device where: the drive mechanism includes a chain conveyor; and the plurality of containers each include a first plug. The multi-station may also include a second plug. The multi-station may also include where each of the first plug and the second plug have a shape that corresponds to an interior passageway of the housing. The sanitizing device further including: where the drive mechanism includes a belt conveyor; and the plurality of containers each include: The sanitizing device may also include a container having a cylindrical body with a hollow center. The sanitizing device may also include a bottom portion defined by the housing. The sanitizing device where the first sanitation station includes a radio frequency transmitter. The sanitizing device where the first sanitizing station includes: means for dispensing a first sanitizing agent; and where the first sanitizing agent is selected from the group including of: The sanitizing device may also include ozone gas, microwave radiation, acidification agents, and ultraviolet light. The sanitizing device where the receiving station is adjacent to the dispensing station. The sanitizing device where the drive mechanism is configured for intermittent motion. The sanitizing device where a second sanitizing station includes an ultraviolet light source disposed along the path. The sanitizing device including a means for flooding the first container with ozone gas. Implementations of the described techniques may include hardware, a method or process, or computer software on a computer-accessible medium.

One general aspect includes a method for reducing *E. coli* and *Salmonella* of successive pre-measured units of a particulate animal feed without substantially increasing the head height requirement of a feed production system, the method including: moving a plurality of containers about a path within a housing, the path including a receiving station, a sanitizing station, and a dispensing station, where the receiving station is adjacent to the dispensing station; receiving a pre-measured unit of the particulate animal feed at the receiving station into the plurality of containers; exposing the pre-measured unit of the particulate animal feed to two or more sanitizing agents at the sanitizing station; dispensing the pre-measured unit of the particulate animal feed at the dispensing station; repeating the steps of receiving, exposing, and dispensing for successive pre-measured units of the particulate animal feed. Other embodiments of this aspect include corresponding computer systems, apparatus, and computer programs recorded on one or more computer storage devices, each configured to perform the actions of the methods.

FIG. 9 is a flow chart showing a method 900 for successively sanitizing pre-quantified units of flowable food products. Method 900 comprises positioning a first container at the filling station, wherein the first container comprises an open space between a first plug and a second plug of a drag chain conveyor, according to step 902. According to step 904, a first unit of a flowable food product is received directly into the first container at a filling station, the first unit being discrete and pre-measured. According to step 906, the first unit in the first container is moved along a path. According to step 908, an ultraviolet light source is provided to generate an ultraviolet radiation as the first sanitizing agent. According to step 910, the first unit is exposed to the first sanitizing agent at a first sanitizing station disposed along the path. According to step 912, the ultraviolet radiation is admitted into the first container through a wall of the first container. According to 914, the first container is flooded with a fluid sanitizing agent at a second sanitizing station disposed along the path. According to step 916, the fluid sanitizing agent is admitted into the first container through a plurality of perforations in a wall of the first container. According to step 918, the first container is exposed to a discharge aperture to dispense the first unit of the flowable food product under the force of gravity. According to step 920, the first unit is dispensed from the first container for subsequent packaging at a dispensing station disposed along the path.

FIG. 10 shows a process 1000 for successively sanitizing pre-quantified units of flowable food products. According to step 1002, a plurality of containers are moved about a path within a housing, the path comprising a receiving station, a sanitizing station, and a dispensing station, wherein the receiving station is adjacent to the dispensing stations. According to step 1004, a pre-measured unit of the flowable food product is received at the receiving station into a first container. According to step 1006, the pre-measured unit of the flowable food product is exposed to two or more sanitizing agents at the sanitizing station. According to step 1008, the pre-measured unit of the flowable food product is dispensed from the first container at the dispensing station. According to step 1010, the steps of receiving, exposing, and dispensing are repeated for successive pre-measured units of the flowable food product within the first container.

FIG. 11 shows process 1100 depicted as a flow chart for a food sanitizing process. According to step 1102, a first unit of a flowable food product is received directly into a first container at a filling station, the first unit being a discrete quantity measured for packaging. According to step 1104, the first unit in the first container is circuited along a path. According to step 1106, the first unit is exposed to a first sanitizing agent at a first sanitizing station disposed along the path. According to step 1108, the first unit is dispensed from the first container at a dispensing station disposed along the path. According to step 1110, the first container is returned to the filling station for refilling with a second unit of the flowable food product. Optionally, process 1100 may also include the step of exposing the first container to a discharge aperture to dispense the first unit of the flowable food product under the force of gravity at the dispensing station. Optionally, process 1100 may also include the step of flooding the first container with a fluid sanitizing agent at a second sanitizing station disposed along the path. Optionally, process 1100 may also include the step of admitting the fluid sanitizing agent into the first container through a plurality of perforations in a wall of the first container, wherein the wall extends vertically between a top portion and a bottom portion of a housing. Optionally, the fluid sanitizing agent of process 1110 comprises ozone gas. Optionally, process 1100 may also include the step of providing an ultraviolet light source mounted to a housing and along the path to generate an ultraviolet radiation as the first sanitizing agent. Optionally, process 1100 may also include the step of admitting the ultraviolet radiation into the first container through a wall of the first container. Optionally, process 1100 may also include the step of positioning the first container at the filling station prior to the step of receiving the first unit of the flowable food product, wherein the first container comprises an open space between a first plug and a second plug of a drag chain conveyor.

FIG. 12 shows process 1200 depicted as a flow chart for sanitizing a plurality of units of a flowable food product, pre-measured for packaging. According to step 1202, a first unit of the plurality of units of the flowable food product is received at the receiving station into a first container. According to step 1204, the first unit of the flowable food product is sanitized with a sanitizing agent at the sanitizing station. According to step 1206, the first unit of the flowable food product is dispensed from the first container at the dispensing station. According to step 1208, the steps of receiving, exposing, and dispensing are repeated for a second unit of the flowable food product within the first container.

It is understood that other embodiments will become readily apparent to those skilled in the art from the following detailed description, wherein various embodiments are shown and described by way of illustration only. As will be realized, the concepts are capable of other and different embodiments and their several details are capable of modification in various other respects, all without departing from the spirit and scope of what is claimed as the invention. Accordingly, the drawings and detailed description are to be regarded as illustrative in nature and not as restrictive.

What is claimed is:

1. A sanitizing process comprising the steps of:
   a. sanitizing a flowable food product;
   b. dividing the flowable food product into a first unit that is measured for packaging;
   c. receiving the first unit into a sanitizing device at a receiving station;
   d. moving the first unit along a circuitous path within the sanitizing device;
   e. exposing the first unit to a plurality of sanitizing agents disposed along the circuitous path; and
   f. dispensing the first unit at a dispensing station disposed along the circuitous path.

2. The sanitizing process of claim 1, further comprising:
   a. containing the first unit within a first container within the sanitizing device; and
   b. returning the first container to the receiving station to be refilled with a second unit of the flowable food product.

3. The sanitizing process of claim 1, further comprising the steps of:
   a. flooding a first container containing the first unit with a fluid sanitizing agent at a first sanitizing station along the circuitous path.

4. The sanitizing process of claim 3, wherein the fluid sanitizing agent comprises ozone gas.

5. The sanitizing process of claim 3, further comprising the step of:
   a. exposing the first unit to ultraviolet light at a second sanitizing station along the circuitous path.

6. The sanitizing process of claim 5, further comprising the step of:
   a. admitting ultraviolet light into the first container through a wall of the first container.

7. The sanitizing process of claim 1, wherein the dispensing station is disposed at the same vertical height as the receiving station.

8. The sanitizing process of claim 1, further comprising the step of:
   a. installing the sanitizing device to an existing food processing system without increasing the head height of the existing food processing system, wherein the sanitizing device is positioned between (1) a first device that divides the flowable food product into a plurality of units that are measured for packaging and (2) a second device that packages the first unit.

9. A sanitizing process comprising the steps of:
   a. receiving a first unit of a pre-sanitized flowable food product that is measured for packaging into a sanitizing device; and
   b. increasing a retention time of the first unit within the sanitizing device by moving a plurality of containers in a circuitous path within the sanitizing device between a receiving station and a dispensing station adjacent to and downstream from the receiving station.

10. The sanitizing process of claim 9 further comprising the step of:
    a. maintaining the first unit as a discrete unit between the receiving station and the dispensing station.

11. The sanitizing process of claim 10 further comprising the step of:
   a. sanitizing the first unit with a plurality of sanitizing agents within the sanitizing device during the retention time.

12. The sanitizing process of claim 11, further comprising the step of:
   a. repeating the steps of receiving, maintaining, and sanitizing for a second unit of the pre-sanitized flowable food product within a first container, which is the first container that contained the first unit.

13. The sanitizing process of claim 9, wherein the circuitous path is primarily horizontal.

14. The sanitizing process of claim 9 further comprising the step of:
   a. dispensing the first unit at approximately the same vertical height as the first unit is received into the sanitizing device.

15. The sanitizing process of claim 9 further comprising the steps of:
   a. moving the first unit vertically within the sanitizing device; and
   b. returning the first unit to the vertical height of the receiving station upon entering the dispensing station.

16. The sanitizing process of claim 9, further comprising the step of:
   a. installing the sanitizing device to an existing food processing system without increasing the head height of the existing food processing system, wherein the sanitizing device is positioned between (1) a first device for dividing the pre-sanitized flowable food product into a plurality of units that are measured for packaging and (2) a second device for packaging.

17. A sanitizing process comprising the steps of:
   a. moving a first container in a circuitous path within a sanitizing device between a receiving station and a dispensing station;
   b. flooding the first container with a fluid sanitizing agent at a first sanitizing station along the circuitous path;
   c. exposing the first container to ultraviolet light at a second sanitizing station along the circuitous path; and
   d. returning the first container to the dispensing station disposed at the same vertical height as the receiving station.

18. The sanitizing process of claim 17 further comprising the step of:
   a. pre-sanitizing a flowable food product;
   b. dividing the flowable food product into a first unit that is measured for packaging; and
   c. receiving the first unit into the first container within the sanitizing device.

19. The sanitizing process of claim 18, wherein the dispensing station is adjacent to and downstream from the receiving station.

20. The sanitizing process of claim 17, further comprising:
   a. installing the sanitizing device to an existing food processing system without increasing the head height of the existing food processing system, wherein the sanitizing device is positioned between (1) a first device for dividing a flowable food product into a first unit that is measured for packaging and (2) a second device for packaging.

* * * * *